(12) United States Patent
Schwammberger et al.

(10) Patent No.: US 9,474,557 B2
(45) Date of Patent: Oct. 25, 2016

(54) INTRAMEDULLARY NAIL

(71) Applicant: ZIMMER GMBH, Winterthur (CH)

(72) Inventors: Andy Schwammberger, Holstein (CH);
Jordan Velikov, Horgen (CH); Reto Senger, Winterthur (CH); Rolf Dittmann, Nussbaumen (CH)

(73) Assignee: Zimmer GmbH, Winterthur (CH)

( * ) Notice: Subject to any disclaimer, the term of this patent is extended or adjusted under 35 U.S.C. 154(b) by 288 days.

(21) Appl. No.: 14/158,946

(22) Filed: Jan. 20, 2014

(65) Prior Publication Data

US 2014/0135767 A1 May 15, 2014

Related U.S. Application Data

(63) Continuation of application No. 12/578,038, filed on Oct. 13, 2009, now Pat. No. 8,668,695.

(60) Provisional application No. 61/105,583, filed on Oct. 15, 2008.

(51) Int. Cl.
*A61B 17/56* (2006.01)
*A61B 17/72* (2006.01)
*A61B 17/74* (2006.01)

(52) U.S. Cl.
CPC ......... *A61B 17/7283* (2013.01); *A61B 17/744* (2013.01); *A61B 17/7291* (2013.01)

(58) Field of Classification Search
CPC .................. A61B 17/7283; A61B 17/744
See application file for complete search history.

(56) References Cited

U.S. PATENT DOCUMENTS

| | | | |
|---|---|---|---|
| 2,239,088 A | 4/1941 | Ettinger | |
| 2,518,019 A | 8/1950 | Kane | |
| 3,433,220 A | 3/1969 | Zickel | |
| 3,996,931 A | 12/1976 | Callender, Jr. | |
| 4,103,683 A | 8/1978 | Neufeld | |

(Continued)

FOREIGN PATENT DOCUMENTS

| | | |
|---|---|---|
| CN | 2362450 Y | 2/2000 |
| CN | 2471292 Y | 1/2002 |

(Continued)

OTHER PUBLICATIONS

"Korean Application Serial No. 520050165305, Notice of Preliminary Rejection ailed Oct. 21, 2015", 7 pgs.

(Continued)

*Primary Examiner* — Jan Christopher Merene
*Assistant Examiner* — Atiya Mahmud
(74) *Attorney, Agent, or Firm* — Schwegman Lunberg & Woessner, P.A.

(57) ABSTRACT

The present invention provides an intramedullary nail having a body with a transverse bore extending through the body and having an area of enhanced stress distribution on at least the lateral side of the transverse bore. In one exemplary embodiment, the intramedullary nail includes a cutout adjacent to the transverse bore, such as an oblique cutout, that enhances the stress distribution of the intramedullary nail in the region around the lateral opening of the transverse bore. In one exemplary embodiment, the cutout includes a ramp portion or area that defines the lateral opening of the transverse bore. In other exemplary embodiments, the cutout includes a runout or a substantially flat portion that defines the lateral opening of the transverse bore.

12 Claims, 8 Drawing Sheets

(56) References Cited

U.S. PATENT DOCUMENTS

| | | |
|---|---|---|
| 4,493,317 A | 1/1985 | Klaue |
| 4,506,662 A | 3/1985 | Anapliotis |
| 4,622,959 A | 11/1986 | Marcus |
| 4,776,330 A | 10/1988 | Chapman et al. |
| 4,805,607 A | 2/1989 | Engelhardt et al. |
| 4,817,591 A | 4/1989 | Klaue |
| 4,827,917 A | 5/1989 | Brumfield |
| 4,846,162 A | 7/1989 | Moehring |
| 4,875,474 A | 10/1989 | Border |
| 4,875,475 A | 10/1989 | Comte et al. |
| 4,895,572 A | 1/1990 | Chernoff |
| 4,976,258 A | 12/1990 | Richter et al. |
| 4,978,349 A | 12/1990 | Frigg |
| 4,981,481 A | 1/1991 | Kranz et al. |
| 5,032,125 A | 7/1991 | Durham et al. |
| 5,034,013 A | 7/1991 | Kyle et al. |
| 5,041,114 A | 8/1991 | Chapman et al. |
| 5,041,115 A | 8/1991 | Frigg et al. |
| 5,057,103 A | 10/1991 | Davis |
| 5,057,110 A | 10/1991 | Kranz et al. |
| 5,066,296 A | 11/1991 | Chapman et al. |
| 5,112,333 A | 5/1992 | Fixel |
| 5,122,141 A | 6/1992 | Simpson et al. |
| 5,167,663 A | 12/1992 | Brumfield |
| 5,176,681 A | 1/1993 | Lawes et al. |
| 5,201,735 A | 4/1993 | Chapman et al. |
| 5,312,406 A | 5/1994 | Brumfield |
| 5,356,410 A | 10/1994 | Pennig |
| 5,364,398 A | 11/1994 | Chapman et al. |
| 5,397,328 A | 3/1995 | Behrens et al. |
| 5,489,284 A | 2/1996 | James et al. |
| 5,499,986 A | 3/1996 | Dimarco |
| 5,531,748 A | 7/1996 | De La Caffiniere |
| 5,549,610 A | 8/1996 | Russell et al. |
| 5,562,667 A | 10/1996 | Shuler et al. |
| 5,573,536 A | 11/1996 | Grosse et al. |
| 5,578,035 A | 11/1996 | Lin |
| 5,620,445 A | 4/1997 | Brosnahan et al. |
| 5,653,709 A | 8/1997 | Frigg |
| 5,658,287 A | 8/1997 | Hofmann et al. |
| 5,658,288 A | 8/1997 | Kim |
| 5,658,339 A | 8/1997 | Tronzo et al. |
| 5,713,902 A | 2/1998 | Friedl |
| 5,743,908 A | 4/1998 | Kim |
| 5,766,174 A | 6/1998 | Perry |
| 5,772,662 A | 6/1998 | Chapman et al. |
| 5,779,704 A | 7/1998 | Kim |
| 5,855,579 A | 1/1999 | James et al. |
| 5,928,235 A | 7/1999 | Friedl |
| 5,973,223 A | 10/1999 | Tellman et al. |
| 6,010,506 A | 1/2000 | Gosney et al. |
| 6,019,761 A | 2/2000 | Gustilo |
| 6,022,352 A | 2/2000 | Vandewalle |
| 6,034,295 A | 3/2000 | Rehberg et al. |
| 6,106,528 A | 8/2000 | Durham et al. |
| 6,123,708 A | 9/2000 | Kilpela et al. |
| 6,168,595 B1 | 1/2001 | Durham et al. |
| 6,210,414 B1 | 4/2001 | Lin |
| 6,221,074 B1 | 4/2001 | Cole et al. |
| 6,224,601 B1 | 5/2001 | Friedl |
| 6,228,086 B1 | 5/2001 | Wahl et al. |
| 6,231,576 B1 | 5/2001 | Frigg et al. |
| 6,235,031 B1 | 5/2001 | Hodgeman et al. |
| 6,261,290 B1 | 7/2001 | Friedl |
| 6,270,499 B1 | 8/2001 | Leu et al. |
| 6,296,645 B1 | 10/2001 | Hover et al. |
| 6,319,253 B1 | 11/2001 | Ackeret et al. |
| 6,322,562 B1 | 11/2001 | Wolter |
| 6,402,753 B1 | 6/2002 | Cole et al. |
| 6,406,477 B1 | 6/2002 | Fujiwara |
| 6,443,954 B1 | 9/2002 | Bramlet et al. |
| 6,461,360 B1 | 10/2002 | Adam |
| 6,488,684 B2 | 12/2002 | Bramlet et al. |
| 6,547,791 B1 | 4/2003 | Buhren et al. |
| 6,558,388 B1 | 5/2003 | Bartsch et al. |
| 6,569,165 B2 | 5/2003 | Wahl et al. |
| 6,579,293 B1 | 6/2003 | Chandran |
| 6,648,889 B2 | 11/2003 | Bramlet et al. |
| 6,706,046 B2 | 3/2004 | Orbay |
| 6,783,530 B1 | 8/2004 | Levy |
| 6,786,908 B2 | 9/2004 | Hover et al. |
| 6,808,527 B2 | 10/2004 | Lower et al. |
| 6,835,197 B2 | 12/2004 | Roth et al. |
| 6,855,146 B2 | 2/2005 | Frigg et al. |
| 6,921,400 B2 | 7/2005 | Sohngen |
| 6,926,719 B2 | 8/2005 | Sohngen et al. |
| 6,932,818 B2 | 8/2005 | Behrens |
| 6,932,819 B2 | 8/2005 | Wahl et al. |
| 6,981,976 B1 | 1/2006 | Schoenefeld |
| 7,001,386 B2 | 2/2006 | Sohngen et al. |
| 7,008,425 B2 | 3/2006 | Phillips |
| 7,018,380 B2 | 3/2006 | Cole |
| 7,041,104 B1 | 5/2006 | Cole et al. |
| 7,066,946 B2 | 6/2006 | Douk et al. |
| 7,182,765 B2 | 2/2007 | Roth et al. |
| 7,232,442 B2 | 6/2007 | Sohngen et al. |
| 7,232,443 B2 | 6/2007 | Zander et al. |
| 7,247,171 B2 | 7/2007 | Sotereanos |
| 7,670,340 B2 * | 3/2010 | Brivio et al. .................. 606/64 |
| 7,763,022 B2 | 7/2010 | Speitling et al. |
| D638,125 S | 5/2011 | Velikov |
| D638,126 S | 5/2011 | Velikov |
| 8,157,803 B1 | 4/2012 | Zirkle, Jr. et al. |
| 8,668,695 B2 | 3/2014 | Schwammberger et al. |
| 2001/0012939 A1 | 8/2001 | Wahl et al. |
| 2002/0029041 A1 | 3/2002 | Hover et al. |
| 2002/0032445 A1 | 3/2002 | Fujiwara |
| 2002/0103488 A1 | 8/2002 | Lower et al. |
| 2002/0107578 A1 | 8/2002 | Speitling et al. |
| 2002/0111629 A1 | 8/2002 | Phillips |
| 2002/0133156 A1 | 9/2002 | Cole |
| 2002/0151897 A1 | 10/2002 | Zirkle, Jr. |
| 2002/0151898 A1 | 10/2002 | Sohngen et al. |
| 2002/0156473 A1 | 10/2002 | Bramlet et al. |
| 2003/0004514 A1 | 1/2003 | Frigg et al. |
| 2003/0018336 A1 | 1/2003 | Vandewalle |
| 2003/0069581 A1 | 4/2003 | Stinson et al. |
| 2003/0074000 A1 | 4/2003 | Roth et al. |
| 2003/0114855 A1 | 6/2003 | Wahl et al. |
| 2003/0171819 A1 | 9/2003 | Sotereanos |
| 2003/0195515 A1 | 10/2003 | Sohngen |
| 2004/0153073 A1 | 8/2004 | Orbay |
| 2004/0158249 A1 | 8/2004 | Roth et al. |
| 2004/0172027 A1 | 9/2004 | Speitling et al. |
| 2004/0260290 A1 | 12/2004 | Zander et al. |
| 2005/0010223 A1 | 1/2005 | Gotfried |
| 2005/0055023 A1 | 3/2005 | Sohngen et al. |
| 2005/0055024 A1 | 3/2005 | James et al. |
| 2005/0065520 A1 | 3/2005 | Orbay |
| 2005/0065528 A1 | 3/2005 | Orbay |
| 2005/0069397 A1 | 3/2005 | Shavit et al. |
| 2005/0070903 A1 | 3/2005 | Roth et al. |
| 2005/0075637 A1 | 4/2005 | Semet |
| 2005/0080335 A1 | 4/2005 | Simon et al. |
| 2005/0101959 A1 | 5/2005 | Mitkovic |
| 2005/0143739 A1 | 6/2005 | Shinjo et al. |
| 2005/0149024 A1 | 7/2005 | Ferrante et al. |
| 2005/0149025 A1 | 7/2005 | Ferrante et al. |
| 2005/0159749 A1 | 7/2005 | Levy et al. |
| 2005/0203510 A1 | 9/2005 | Sohngen |
| 2005/0273103 A1 | 12/2005 | Wahl et al. |
| 2005/0277936 A1 | 12/2005 | Siravo et al. |
| 2005/0283154 A1 | 12/2005 | Orbay et al. |
| 2006/0015101 A1 | 1/2006 | Warburton et al. |
| 2006/0069392 A1 | 3/2006 | Brivio et al. |
| 2006/0084997 A1 | 4/2006 | Dejardin |
| 2006/0084984 A1 | 4/2006 | Aschmann |
| 2006/0095039 A1 * | 5/2006 | Mutchler .................. 606/64 |
| 2006/0106384 A1 | 5/2006 | Reber et al. |
| 2006/0106389 A1 | 5/2006 | Reber et al. |
| 2006/0111716 A1 | 5/2006 | Schlienger et al. |
| 2006/0111717 A1 | 5/2006 | Saueressig et al. |
| 2006/0122600 A1 | 6/2006 | Cole |
| 2006/0142763 A1 | 6/2006 | Munro et al. |

(56) References Cited

U.S. PATENT DOCUMENTS

| | | |
|---|---|---|
| 2006/0149247 A1 | 7/2006 | Frigg et al. |
| 2006/0149248 A1 | 7/2006 | Schlienger et al. |
| 2006/0149257 A1 | 7/2006 | Orbay et al. |
| 2006/0161155 A1 | 7/2006 | Schlienger et al. |
| 2006/0161156 A1 | 7/2006 | Orbay |
| 2006/0173457 A1 | 8/2006 | Tornier |
| 2006/0189988 A1 | 8/2006 | Schlienger et al. |
| 2006/0200142 A1 | 9/2006 | Sohngen et al. |
| 2006/0200143 A1 | 9/2006 | Warburton |
| 2006/0200160 A1* | 9/2006 | Border et al. ............... 606/88 |
| 2006/0235394 A1 | 10/2006 | Martin |
| 2006/0235395 A1 | 10/2006 | Frigg et al. |
| 2006/0241604 A1 | 10/2006 | Frigg et al. |
| 2006/0241605 A1 | 10/2006 | Schlienger et al. |
| 2006/0264943 A1 | 11/2006 | Chieng |
| 2006/0264944 A1 | 11/2006 | Cole |
| 2007/0016203 A1 | 1/2007 | Schlienger et al. |
| 2007/0049938 A1 | 3/2007 | Wallace et al. |
| 2007/0049939 A1 | 3/2007 | Wallace et al. |
| 2007/0049940 A1 | 3/2007 | Wallace et al. |
| 2007/0100342 A1 | 5/2007 | Green et al. |
| 2007/0100343 A1 | 5/2007 | Cole et al. |
| 2007/0123876 A1 | 5/2007 | Czartoski et al. |
| 2007/0233104 A1 | 10/2007 | Metzinger |
| 2007/0270845 A1 | 11/2007 | Watanabe et al. |
| 2008/0058813 A1 | 3/2008 | Gotfried |
| 2008/0058814 A1 | 3/2008 | Gotfried |
| 2008/0119856 A1 | 5/2008 | Gotfried |
| 2008/0195098 A1 | 8/2008 | Gotfried |
| 2008/0249580 A1 | 10/2008 | Evans et al. |
| 2009/0048600 A1* | 2/2009 | Matityahu et al. ............ 606/64 |
| 2010/0174284 A1 | 7/2010 | Schwammberger et al. |
| 2010/0179551 A1 | 7/2010 | Keller et al. |
| 2013/0274746 A1* | 10/2013 | Peyrot et al. ................. 606/63 |

FOREIGN PATENT DOCUMENTS

| | | |
|---|---|---|
| DE | 4318150 A1 | 12/1994 |
| EP | 251583 A2 | 1/1988 |
| EP | 0257118 A1 | 3/1988 |
| EP | 0306709 A2 | 8/1988 |
| EP | 0471418 A1 | 2/1992 |
| EP | 0306709 B1 | 12/1992 |
| EP | 0517435 A1 | 12/1992 |
| EP | 1363545 A1 | 11/2003 |
| EP | 1452144 A2 | 9/2004 |
| EP | 1522268 A1 | 4/2005 |
| FR | 2668360 A1 | 4/1992 |
| JP | 2295556 A | 12/1990 |
| JP | 5237136 A | 9/1993 |
| JP | 7222753 A | 8/1995 |
| JP | 2000051224 A | 2/2000 |
| JP | 2004237108 A | 8/2004 |
| JP | 2007268279 A | 10/2007 |
| JP | 2008036094 A | 2/2008 |
| WO | WO-9920195 A1 | 4/1999 |
| WO | WO-9944528 A1 | 8/1999 |
| WO | WO-0015127 A1 | 3/2000 |
| WO | WO-0280790 A1 | 10/2002 |
| WO | WO-03030749 A1 | 4/2003 |
| WO | WO-2004002342 A2 | 1/2004 |
| WO | WO-2005122932 A2 | 12/2005 |
| WO | WO-2006105685 A2 | 10/2006 |
| WO | WO-2007009123 A2 | 1/2007 |
| WO | WO-2007023101 A1 | 3/2007 |
| WO | WO-2008147975 A1 | 12/2008 |

OTHER PUBLICATIONS

"U.S. Appl. No. 12/578,038, Decision on Pre-Appeal Brief Request mailed Mar. 6, 2013", 2 pgs.

"U.S. Appl. No. 12/578,038, Final Office Action mailed Sep. 26, 2012", 14 pgs.

"U.S. Appl. No. 12/578,038, Non Final Office Action mailed May 10, 2012", 12 pgs.

"U.S. Appl. No. 12/578,038, Non Final Office Action mailed Oct. 21, 2011", 17 pgs.

"U.S. Appl. No. 12/578,038, Notice of Allowance mailed Jun. 25, 2013", 10 pgs.

"U.S. Appl. No. 12/578,038, Notice of Allowance mailed Nov. 15, 2013", 11 pgs.

"U.S. Appl. No. 12/578,038, Pre-Appeal Brief Request filed Jan. 23, 2013", 5 pgs.

"U.S. Appl. No. 12/578,038, Response filed Jan. 23, 2012 to Non Final Office Action mailed Oct. 21, 2011", 11 pgs.

"U.S. Appl. No. 12/578,038, Response filed Sep. 6, 2012 to Non Final Office Action mailed May 10, 2012", 11 pgs.

"U.S. Appl. No. 12/578,038, Supplemental Response filed Mar. 22, 2012 to Non Final Office Action mailed Oct. 21, 2011", 6 pgs.

"Chinese Application No. 200980140511.0, Office Action mailed Jul. 23, 2013", (W/ English Translation), 6 pgs.

"Chinese Application No. 200980140511.0, Office Action mailed Dec. 12, 2012", (W/ English Translation), 13 pgs.

"European Application No. 09740851.2, Office Action mailed Jul. 5, 2012", 5 pgs.

"International Application No. PCT/EP2009/007353, International Preliminary Report on Patentability mailed Jan. 18, 2011", 14 pgs.

"International Application No. PCT/EP2009/007353, International Search Report mailed Jan. 26, 2010", 2 pgs.

"International Application No. PCT/EP2009/007353, Written Opinion mailed Jan. 26, 2010", 7 pgs.

"International Application No. PCT/US2008/064680, International Preliminary Report on Patentability mailed Dec. 1, 2009", 23 pgs.

"Japanese Application No. 2011-531392, Office Action mailed Jul. 9, 2003", (W/English Translation), 9 pgs.

Leung, Kwok S, et al., "Gamma3 Trochanteric Nail 180", Operative Technique, Stryker, (2004), 48 pgs.

* cited by examiner

INTRAMEDULLARY NAIL

CROSS REFERENCE TO RELATED APPLICATION

This application is a continuation of U.S. patent application Ser. No. 12/578,038, filed on Oct. 13, 2009, which claims the benefit under Title 35, U.S.C. §119(e) of U.S. Provisional Patent Application Ser. No. 61/105,583, entitled STRENGTHENED INTRAMEDULLARY NAIL, filed on Oct. 15, 2008, the disclosures of which are expressly incorporated herein by reference in their entireties.

BACKGROUND

1. Field of the Invention

The present invention relates to orthopedic components, and, particularly, to intramedullary nails.

2. Description of the Related Art

Intramedullary nails may be used to align and stabilize fractures of a long bone, such as a femur. In a fractured femur, an intramedullary nail may be inserted into the intramedullary canal of the femur and positioned to extend across the fracture line of the femur. Then, screws or other securement devices may be inserted through bores formed in the intramedullary nail on opposing sides of the fractured femur to secure the opposing portions of the fractured femur together.

If the head and/or neck of a long bone, such as the head and/or neck of the femur, has fractured, a lag screw may be inserted into a transverse bore formed in the intramedullary nail. This bore is aligned so that the lag screw extends through the neck and into the head of the long bone and across the fracture line, allowing the lag screw to reduce the fracture of the neck and/or head of the long bone.

For example, referring to FIG. 1, femur 10 is shown including shaft 12, neck 14, and head 16. As shown, neck 14 of femur 10 has been fractured at line 17. Transverse bore 18 extends through intramedullary nail 20 and is sized to receive lag screw 22 therethrough. Specifically, lag screw 22 has an outer diameter that is slightly smaller than the diameter of transverse bore 18. This allows lag screw 22 to pass through transverse bore 18 and reduce the fracture at line 17.

However, due to the need for lag screw 22 to have an outer diameter that is less than the diameter of transverse bore 18, lag screw 22 will pivot slightly within transverse bore 18 of intramedullary nail 20 when a force is applied to the end of lag screw 22. For example, force FG may be exerted on the end of lag screw 22, which results from head 16 of femur 10 bearing the weight of an individual. When force FG is applied to the end of lag screw 22, lag screw 22 pivots slightly within transverse bore 18 of intramedullary nail 20 to create two support points that bear the resultant forces. First support point 24 is a medial, distal support point, where force FM acts on lag screw 22, and second support point 26 is a lateral, proximal support point, where force FL acts on lag screw 22. By exerting a force on first and second support points 22, 24, force FM induces a compressive stress in the mass of the lower part of intramedullary nail 20, while force FL induces a tensile stress in the region of transverse bore 18. Additionally, force FL acting on support point 26 is amplified by the leverage ratio of lag screw 22 within transverse bore 18. The resulting, theoretical stress distribution is shown in FIG. 3, where the stress is concentrated around the medial and lateral openings of transverse bore 18.

Referring to FIG. 2, which shows a cross-section of intramedullary nail 20, the maximum tension caused by force FL is found near the lateral opening of transverse bore 18, which has sharp edges 27 that are formed in a region with very critical geometry. In addition to the maximum tension occurring at the lateral most side of intramedullary nail 10, the formation of transverse bore 18 in intramedullary nail 20 creates a notch effect that further concentrates stress along sharp edges 27 of the lateral opening of transverse bore 18, where a minimal amount of material is provided. Specifically, the region about the lateral opening of transverse bore 18, for example, has a minimal amount of material positioned thereabove as a result of the shape of intramedullary nail 20. Stated another way, because intramedullary nail 20 has a substantially circular cross-section in a direction perpendicular to the longitudinal axis of intramedullary nail 20 and because the lateral opening to transverse bore 18 is located at an outer edge of intramedullary nail 20, a minimal amount of material is provided in the region of support point 26 and the lateral opening of transverse bore 18, as compared to the amount of material in the region closer to the longitudinal axis of intramedullary nail 20. As a result of having a minimal amount of material in the region of the lateral opening of transverse bore 18, the material in the region of the lateral opening of transverse bore 18 has a greater concentration of stress than the material that is closer to the longitudinal axis of intramedullary nail 20. This requires that intramedullary nail 20 is formed from stronger, more expensive materials in order to withstand the increased concentration of stress in the material adjacent to the lateral opening of transverse bore 18 and/or has an increased size in the region of intramedullary nail 20 near the lateral opening of transverse bore 18 in order to increase the volume of material present and to decrease the concentration of stress adjacent to the lateral opening of transverse bore 18.

SUMMARY

The present invention provides an intramedullary nail having a body with a transverse bore extending through the body and having an area of enhanced stress distribution on at least the lateral side of the transverse bore. In one exemplary embodiment, the intramedullary nail includes a cutout adjacent to the transverse bore, such as an oblique cutout, that enhances the stress distribution of the intramedullary nail in the region around the lateral opening of the transverse bore. In one exemplary embodiment, the cutout includes a ramp portion or area that defines the lateral opening of the transverse bore. In other exemplary embodiments, the ramp portion of the cutout defines a runout or a substantially flat portion that defines the lateral opening of the transverse bore.

Specifically, in forming a cutout adjacent to a transverse bore of an intramedullary nail in accordance with the teachings of the present invention, as set forth in detail below, material positioned on the distal side of the transverse bore and/or adjacent to the lateral opening of the transverse bore is removed. However, the material positioned on the proximal side of the transverse bore is maintained. For example, as compared to traditional intramedullary nails having a substantially cylindrical shape in the area adjacent to the transverse bore, material is absence in the present intramedullary nail in the area directly distal of and/or adjacent to a lateral opening of the transverse bore. By creating an absence of material distal of the transverse bore, the stresses induced at the lateral opening of the intramedullary nail, such as in the area distal of lateral support point 54 (FIG. 4A), are distributed in a direction toward the longitudinal axis of the intramedullary nail. As a result, the stresses introduced at the lateral support point are distributed through a different portion of the intramedullary nail, i.e., through a portion of the intramedullary nail spaced a decreased lateral distance from the longitudinal axis of the intramedullary nail relative to the material directly adjacent to the lateral opening of the transverse bore. This allows for the concentration of the stress at the lateral support point adjacent to the lateral opening of the transverse bore to be decreased, as the stress is borne throughout the body of the intramedullary nail.

In each of the exemplary embodiments of the present invention, the cutout formed in the intramedullary nail lacks a sharp edge at the distal end thereof. Instead, each embodiment of the present invention utilizes a smooth transition zone at the distal end of the cutout. As indicated above, in one exemplary embodiment, the smooth transition zone is formed in the distal portion of the cutout as a runout extending parallel to the axis of the intramedullary nail and terminating at an intermediate portion of the intramedullary nail. In another exemplary embodiment, the distal portion of the cutout forms an oblique surface that terminates distally at the outer surface of a proximal portion of the intramedullary nail and forms an angle with the longitudinal axis of the intramedullary nail. By altering the angle that the oblique, distal surface portion of the cutout forms with the longitudinal axis of the intramedullary nail, the specific stress transfer properties of the intramedullary nail may be correspondingly modified and/or optimized for a particular application.

Further, by replacing a sharp edge at the distal end of the cutout with a smooth transition zone, a portion of the intramedullary nail that is subjected to high, oscillating tensile stresses is removed. Additionally, the intramedullary nail may be readily removed from a patient's body, even if bone ingrowth has occurred in the area of the cutout. Specifically, if cancellous bone tissue grows into the area defined by the cutout, when the intramedullary nail is removed, the surface defining the distal portion of the cutout may temporarily displace the elastic cancellous bone tissue and allow the intramedullary nail to slide smoothly along the displaced bone. Then, once the intramedullary nail is removed, the bone tissue may extend back into the space within the intramedullary canal previously occupied by the intramedullary nail. As a result, trauma to the bone tissue is substantially lessened if the intramedullary nail is removed.

Throughout the present application various positional terms, such as distal, proximal, medial, lateral, anterior, and posterior, will be used in the customary manner when referring to the human anatomy. More specifically, "distal" refers to the area away from the point of attachment to the body, while "proximal" refers to the area near the point of attachment the body. For example, the proximal femur refers to the portion of the femur near the hip, while the distal femur refers to the portion of the femur near the tibia. The terms "medial" and "lateral" are also essentially opposites, where "medial" refers to something situated closer to the middle of the body, while "lateral" refers to something situated closer to the left side or the right side of the body (rather than to the middle of the body). With regard to anterior and posterior, "anterior" refers to something situated closer to the front of the body and "posterior" refers to something situated closer to the rear of the body. Additionally, when anatomical terms are used with specific reference to an orthopedic implant, such as an intramedullary nail, the terms are used with respect to the implant being positioned as intended within the human body, which is shown in the various drawings of the present application.

In one form thereof, the present invention provides an intramedullary nail, including an elongate body including a proximal end, a distal end, a medial side, a lateral side, and a longitudinal axis. The elongate body defines an elongate body periphery. The proximal portion of the elongate body has an interior wall defining a transverse bore extending therethrough. The transverse bore extends from the lateral side to the medial side of the elongate body in a direction transverse to the longitudinal axis of the elongate body. The proximal portion includes a cutout positioned adjacent to the transverse bore on the lateral side of the elongate body. The cutout includes a ledge portion extending in a substantially medial-lateral direction and positioned adjacent to a proximal most edge of the wall defining the transverse bore. The cutout also includes a ramp portion defining a substantially planar surface. The ramp portion forms a ramp angle with the longitudinal axis of the elongate body. The ramp angle is between zero degree and thirty degrees, wherein the ramp portion extends along the longitudinal axis of the elongate body in a distal direction. The ramp portion terminating distally at the elongate body periphery, wherein the ramp portion terminates at a position spaced distally from a distal most edge of the wall defining the transverse bore. The cutout also includes an intermediate portion positioned between the ledge portion and the ramp portion. The intermediate portion has an intermediate portion radius of curvature.

In another form thereof, the present invention provides an intramedullary nail including an elongate body having a proximal end, a distal end, a medial side, a lateral side, and a longitudinal axis. The elongate body includes a distal portion defining the distal end of the elongate body and a transition portion extending proximally from the distal portion along the longitudinal axis. The transition portion has a proximal end having a proximal diameter and a distal end having a distal diameter. The proximal diameter is greater than the distal diameter. The transition portion defines a transition portion periphery. The elongate body also includes a proximal portion extending proximally from the transition portion and defining a proximal end of the elongate body. The proximal portion defines a proximal portion periphery. The proximal portion has a diameter substantially equal to the proximal diameter of the transition portion. The proximal portion has an interior wall defining a transverse bore extending therethrough. The transverse bore extends from the lateral side of the elongate body to the medial side of the elongate body in a direction transverse to the longitudinal axis of the elongate body. The proximal portion has a cutout positioned adjacent to the transverse bore on the lateral side of the elongate body. The cutout defines a derivation from the proximal portion periphery and the transition portion periphery having a volume of at least 100 cubic millimeters.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein.

Corresponding reference characters indicate corresponding parts throughout the several views. The exemplifications set out herein illustrate preferred embodiments of the invention and such exemplifications are not to be construed as limiting the scope of the invention in any manner.

DETAILED DESCRIPTION

Figure 7A:
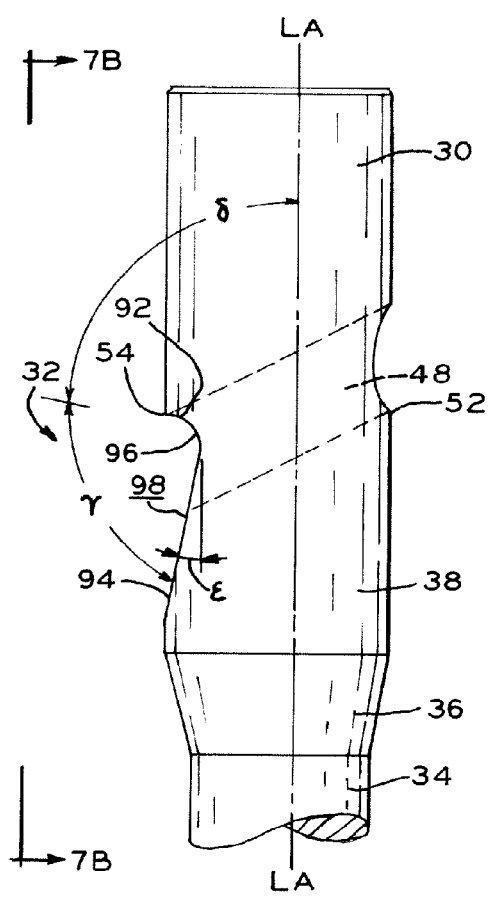
FIG. 7A is a fragmentary, side view of an intramedullary nail of the present invention according to another exemplary embodiment.
Figure 7B:
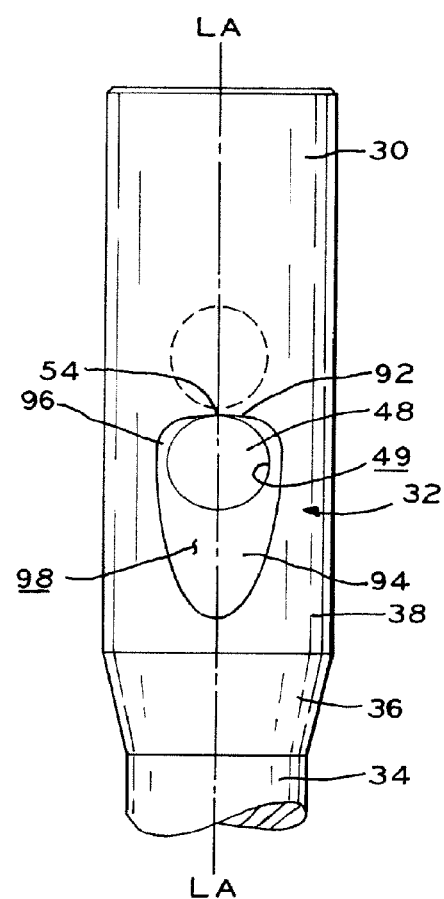
FIG. 7B is a fragmentary view of the intramedullary nail of FIG. 7A taken in the direction of line 7B-7B of FIG. 7A.
Figure 8:
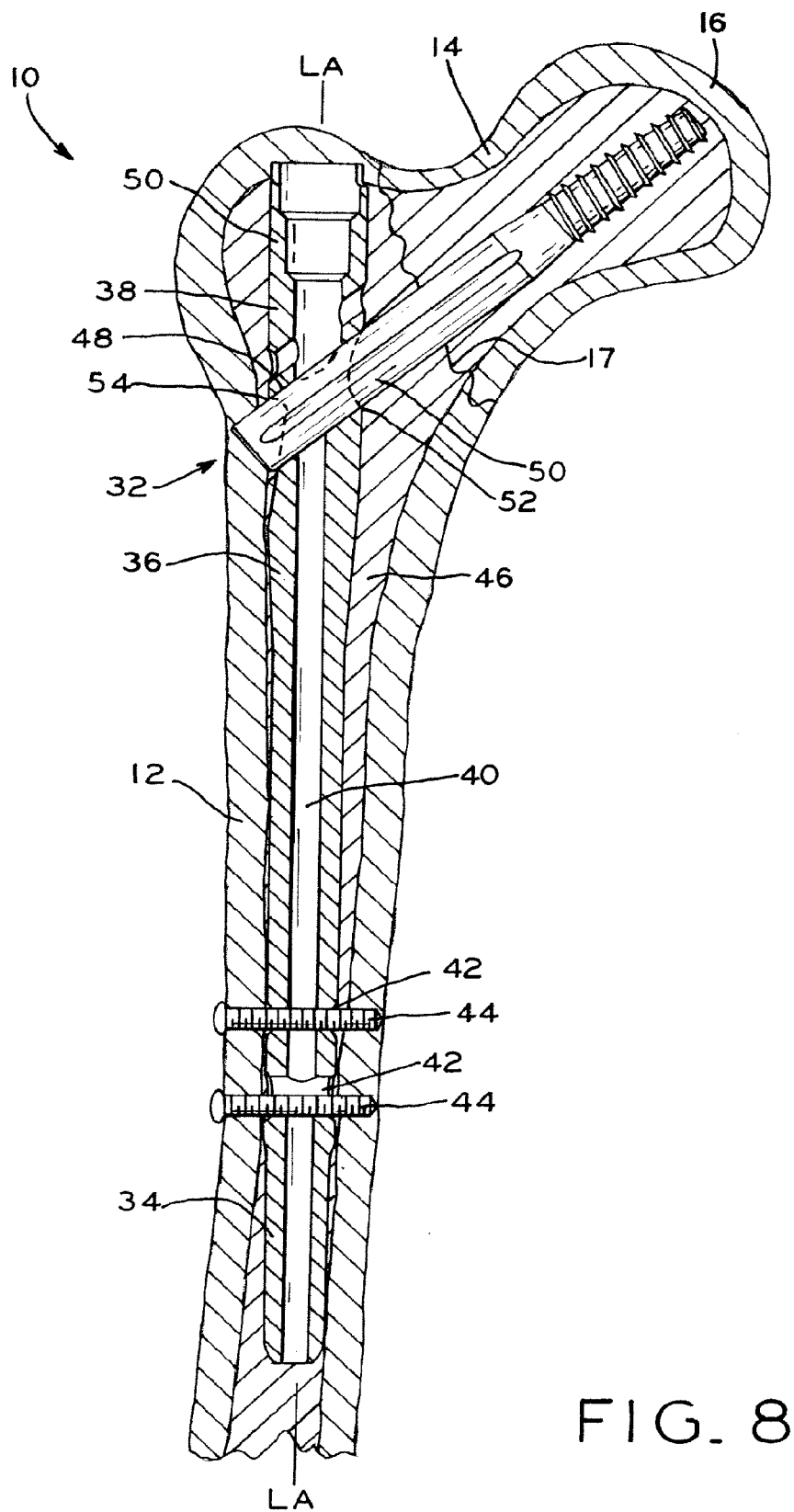
FIG. 8 is a cross-sectional view of the intramedullary nail of FIGS. 7A and 7B positioned within a femur and further depicting fixation screws and a lag screw.
Figure 9:
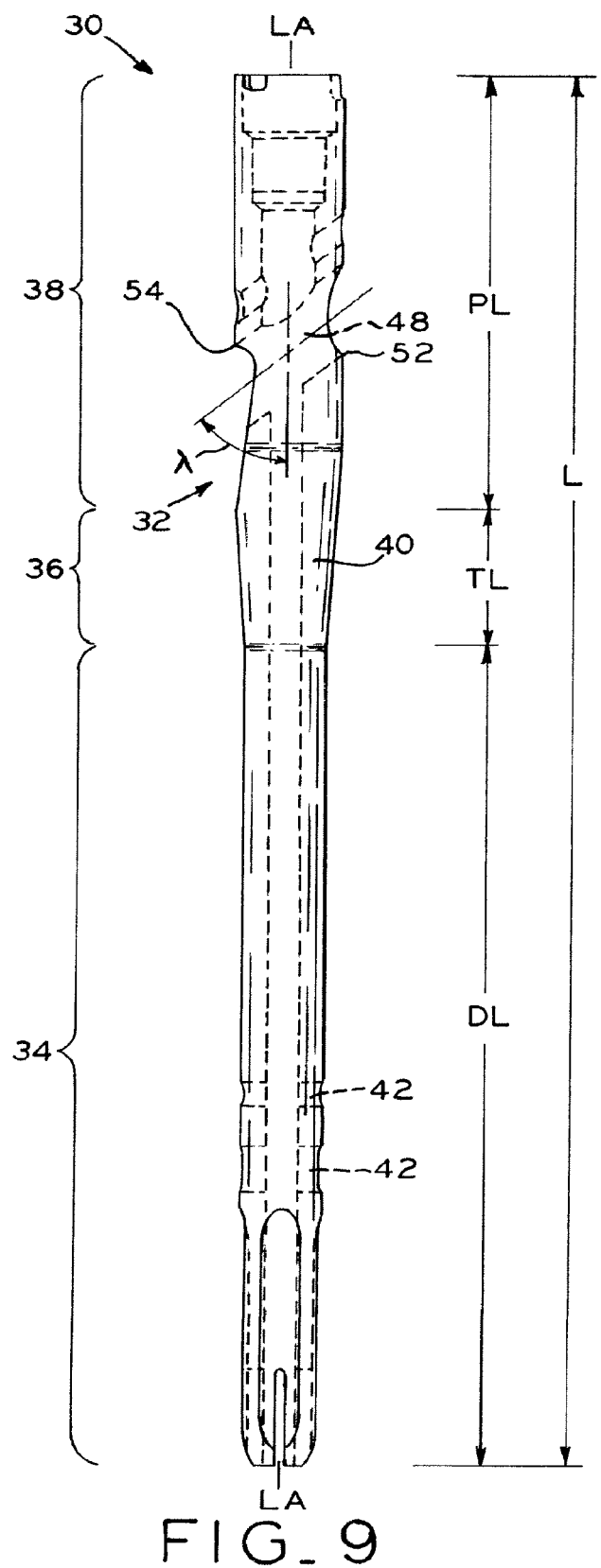
FIG. 9 is a front, side view of the intramedullary nail of FIG. 8.

Referring to FIGS. 8 and 9, intramedullary nail 30 is shown and includes cutout 32 of FIGS. 7A and 7B, as described in detail below. Intramedullary nail 30 forms a substantially cylindrical, elongate body including distal portion 34, transition portion 36, and proximal portion 38. In one exemplary embodiment, longitudinal bore 40 extends along longitudinal axis LA of intramedullary nail 30. Intramedullary nail 30 may be made of a titanium alloy, such as Ti-6Al-4V, or any other biocompatible orthopedic material, such as medical grade stainless steel or a cobalt-chromium alloy. Transverse, distal bores 42 extend through distal portion 34 of intramedullary nail 30 and receive fixation screws 44 therein. Referring to FIG. 8, fixation screws 44 are positioned to extend through transverse bores 42 and are secured to shaft 12 of femur 10. Fixation screws 44 function to prevent rotation within and/or removal of intramedullary nail 30 from intramedullary canal 46 of femur 10.

As shown in FIGS. 8 and 9, in addition to bores 42, proximal portion 38 of intramedullary nail 30 includes wall 49 defining transverse bore 48 through which a lag screw, such as lag screw 50, is positioned. Transverse bore 48 of intramedullary nail 30 is aligned with the axis of neck 14 of femur 10, such that lag screw 50 may be extended through transverse bore 48 and implanted into neck 14 and/or head 16 of femur 10 to reduce a fracture in neck 14 and/or head 16 of femur 10. In exemplary embodiments, intramedullary nail 30 and lag screw 50 may form a collodiaphyseal ("CCD") angle of approximately 125 degrees, 130 degrees, or 135 degrees. While described herein with specific reference to a femur, intramedullary nail 30 may also be used other long bones, such as a tibia, fibula, radius, ulna, and/or clavicle.

In one exemplary embodiment, proximal portion 38 of intramedullary nail 30 defines a proximal end of intramedullary nail 30 and has a proximal diameter. In one exemplary embodiment, the diameter of proximal portion 38 is approximately 15.5 mm. In one exemplary embodiment, proximal portion 38 defines a proximal portion periphery having a substantially cylindrical shape having a diameter equal to the diameter of proximal portion 38 and extending along proximal length PL of proximal portion 38. Referring to FIG. 9, in one exemplary embodiment, distal portion 34 defines a distal end of intramedullary nail 30 and has a distal diameter. In exemplary embodiments, the diameter of distal portion 34 is approximately between 10 mm and 15 mm. In exemplary embodiments, the diameter of distal portion 34 may be equal to approximately 10 mm, 11.5 mm, 13 mm, or 14.5 mm. Transition portion 36 extends between proximal portion 38 and distal portion 34 and provides a substantially conical transition section between proximal portion 38 and distal portion 34. In one exemplary embodiment, transition portion 36 has a distal end having a diameter substantially equal to the diameter of the proximal most portion of distal portion 34 and a proximal end having a diameter substantially equal to the diameter of proximal portion 38. For example, transition portion 36 may have a diameter of approximately 15.5 mm at a proximal end thereof and a diameter of approximately 10 mm at a distal end thereof. In one exemplary embodiment, transition portion 36 defines a transition portion periphery having a substantially conical shape with a proximal diameter equal to the diameter at a proximal end of transition portion 36 and a distal diameter equal to the diameter at a distal end of transition portion 36 and extending along transition portion length TL.

Still referring to FIG. 9, in one exemplary embodiment, the proximal portion 38 of intramedullary nail 30 has a proximal length PL of approximately 58 mm, transition portion 36 has a transition portion length TL of approximately 31 mm, and distal portion 34 of intramedullary nail 30 has a distal portion length DL of between approximately 120 mm and 395 mm. For example, distal portion 34 may have a distal portion length DL as small as approximately 126 mm, 211 mm, 231 mm, 251 mm, or 271 mm and as large as approximately 291 mm, 311 mm, 331 mm, 351 mm, 371 mm, or 391 mm. By combining the overall lengths PL, TL, DL of the proximal portion 38, transition portion 36, and distal portion 34, respectively, the overall length L of intramedullary nail 30 is determined. In one exemplary embodiment, intramedullary nail 30 has an overall length L between approximately 210 mm and approximately 480 mm. For example, intramedullary nail 30 may have a length L as small as approximately 215 mm, 300 mm, 320 mm, 340 mm, or 360 mm and as large as approximately 380 mm, 400 mm, 420 mm, 440 mm, 460 mm, or 480 mm. In one exemplary embodiment, length L is equal to approximately 215 mm.

Referring to transverse bore 48 as shown in FIG. 9, transverse bore 48 of the intramedullary nail 30 forms angle $\lambda$ with longitudinal axis LA of intramedullary nail 30. In one exemplary embodiment, angle $\lambda$ is between approximately 48 degrees and 60 degrees. For example, angle $\lambda$ may be equal to approximately 49 degrees, 54 degrees, or 59 degrees. Referring to longitudinal bore 40, in one exemplary embodiment, longitudinal bore 40 has a diameter of approximately 4.8 mm, except in the area of proximal portion 38 where longitudinal bore 40 may be enlarged to accommodate a set screw (not shown) and/or other components that function to prevent and/or limit translation of lag screw 50 within transverse bore 48 of intramedullary nail 30.

Figure 1:
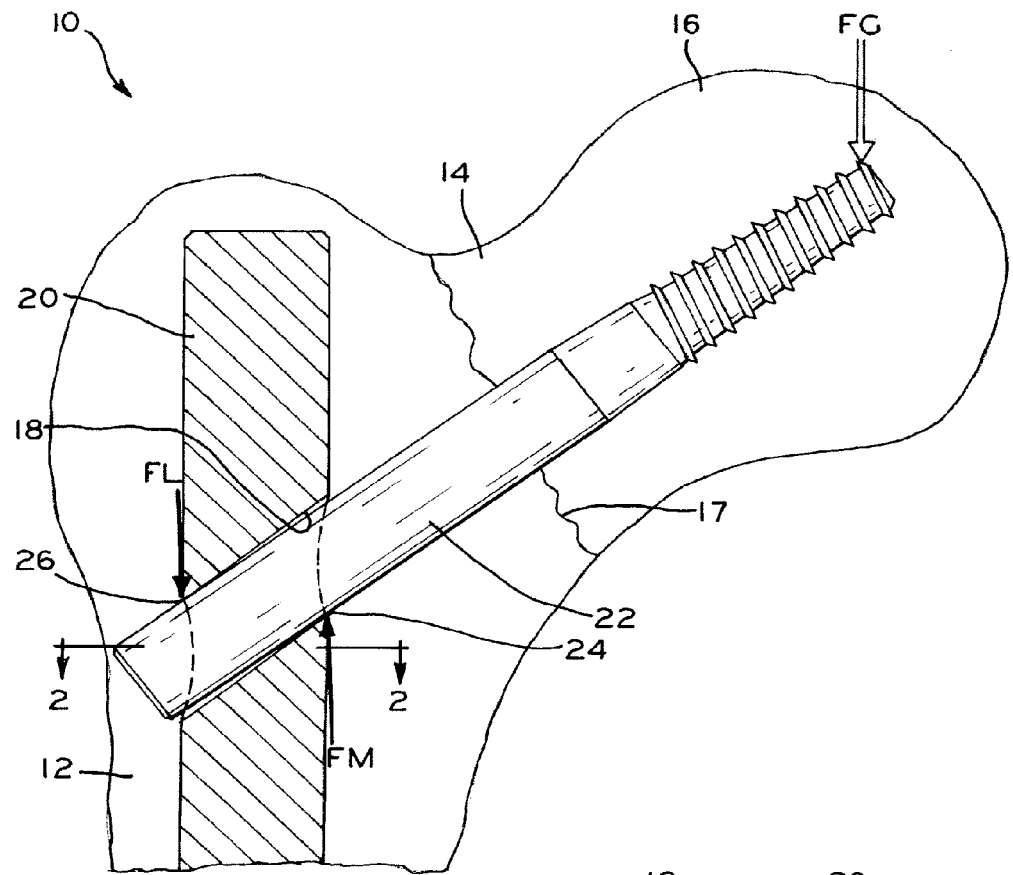
FIG. 1 is a fragmentary, cross-sectional view of a prior art intramedullary nail positioned within a femur and a lag screw extending through a transverse bore of the intramedullary nail to reduce a fracture in the neck of the femur.

As described in detail above with respect to prior art intramedullary nail (FIG. 1), during walking or other movement, a patient's weight may be transferred to the tip of a lag screw, such as lag screw 50 of FIG. 8. As a result, lag screw 50 applies a force to intramedullary nail 30 at medial and lateral support points 52, 54, adjacent to medial and lateral openings of transverse bore 48, respectively. In order to enhance the stress distribution of intramedullary nail 30 in the vicinity of support point 52, the lateral side of proximal portion 38 of intramedullary nail 30 includes a cutout formed therein. As shown in FIGS. 8 and 9, intramedullary nail 30 includes cutout 32, which is described in detail below with respect to FIGS. 7A and 7B. While described and depicted herein with the cutout formed on the lateral side of intramedullary nail 30, the cutout may, in other exemplary embodiments, be formed on both the lateral and the medial sides of intramedullary nail 30 adjacent to the lateral and medial openings of transverse bore 48, respectively.

Additionally, while intramedullary nail 30 is shown as including cutout 32, intramedullary nail 30 may include any of the cutout designs set forth herein, including the use of different cutout designs on the medial and lateral sides of intramedullary nail 30. Further, as used herein, the term "cutout" refers generally to an area of a material in which the cross-section of the material deviates from an otherwise substantially consistent cross-section, but does not require the independent removal of the material. Thus, as used herein, intramedullary nail 30 may be cast or otherwise formed to include a cutout, even though no machining or manufacturing steps were undertaken to remove material from intramedullary nail 30 to form the cutout. Further, the cutouts of the present invention result in the creation of a deviation in the periphery of proximal portion 38, i.e., the proximal portion periphery described above, and/or the periphery of transition portion 36, i.e., the transition portion periphery described above. For example, the derivation in the periphery of proximal portion 38 and transition portion 36 from a cylindrical geometry with a 15.5 mm diameter may be as small as 90 mm$^3$, 95 mm$^3$, 100 mm$^3$, or 105 mm$^3$, and may be as high as 110 mm$^3$, 115 mm$^3$, 120 mm$^3$, or 125 mm$^3$. In one exemplary embodiment, the derivation in the periphery of proximal portion 38 and transition portion 36 from a cylindrical geometry with a 15.5 mm diameter may be equal to substantially 106 mm$^3$.

Figure 2:
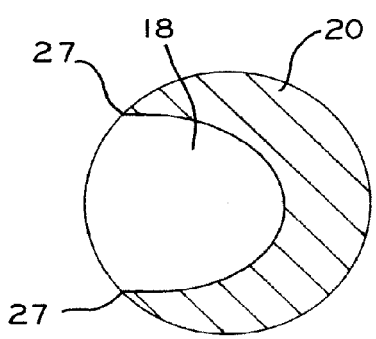
FIG. 2 is a cross-sectional view of the intramedullary nail of FIG. 1 taken along line 2-2 of FIG. 1.
Figure 3:
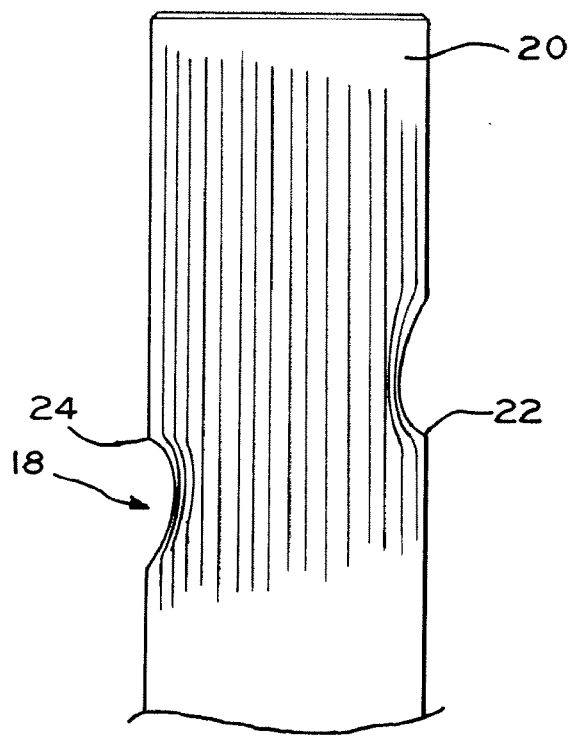
FIG. 3 is a fragmentary, side view of the intramedullary nail of FIG. 1 depicting theoretical stress lines extending therethrough that are created during loading of the lag screw shown in FIG. 1.

In exemplary embodiments, described in detail below, the cutouts of the present invention define ramp portions that form oblique surfaces with respect to the longitudinal axis LA of intramedullary nail 30 or, alternatively, when the ramp portion forms a zero degree angle with longitudinal axis LA of intramedullary nail 30, define runouts that have a surface extending substantially parallel to longitudinal axis LA of intramedullary nail 30. As described in detail below with specific reference to cutout 56 and FIGS. 4A and 4B, these ramp portions or runouts function to reduce the concentration of the stress in the area of the lateral side of transverse bore 48 that is created by the interaction of lag screw 50 with intramedullary nail 30. As a result, intramedullary nail 30 has higher safety margins than similar intramedullary nails, such as those shown in FIGS. 1-3, which are formed in a traditional manner without the cutouts of the present invention.

Figure 4A:
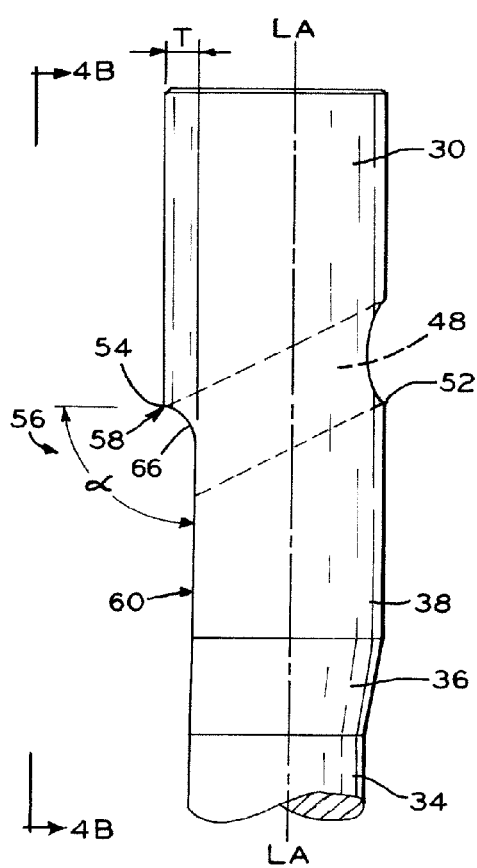
FIG. 4A is a fragmentary, side view of an intramedullary nail of the present invention according to one exemplary embodiment.
Figure 4B:
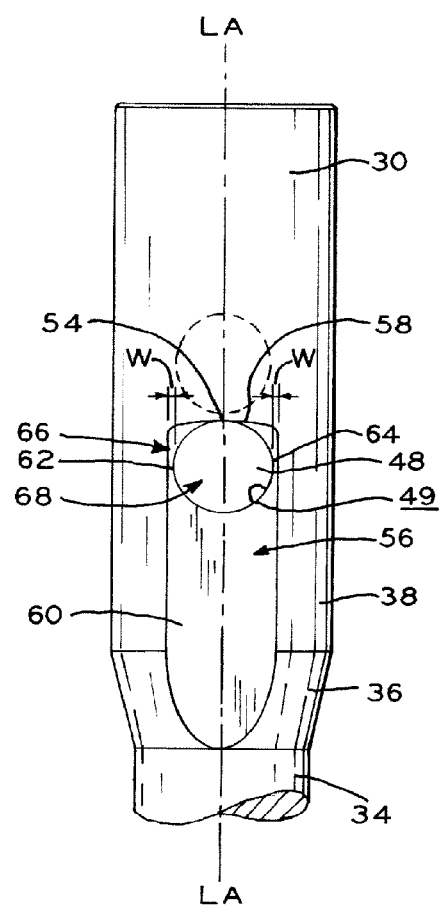
FIG. 4B is a fragmentary view of the intramedullary nail of FIG. 4A taken in the direction of line 4B-4B of FIG. 4A.

Referring to FIGS. 4A and 4B, cutout 56, which is formed according to an exemplary embodiment of the present invention, is shown in conjunction with intramedullary nail 30. Cutout 56 is positioned adjacent to and defines the lateral opening of transverse bore 48. Cutout 56 includes ledge portion 58 and runout portion 60. Runout portion 60 defines a substantially planar surface that extends in a direction substantially parallel to longitudinal axis LA of intramedullary nail 30 and defines flattened sides surfaces 62, 64 on opposing anterior and posterior sides of transverse bore 48. For example, runout portion 60 may form an angle as small as 1 degree, 2 degrees, or 3 degrees with longitudinal axis LA and as large as 177 degrees, 178 degrees, or 179 degrees with longitudinal axis LA. In one exemplary embodiment, flattened side surfaces 62, 64 have a width W of at least substantially 0.2 mm. By ensuring that width W of flattened side surfaces 62, 64 is at least substantially 0.2 mm, a manufacturing tolerance is provide that helps to ensure that flattened side surfaces 62, 64 are properly formed during the manufacturing process.

Ledge portion 58 and runout portion 60 are connected to one another by intermediate portion 66 and are separated from one another by angle α. In one exemplary embodiment, intermediate portion 66 has a radius of curvature of approximately 3 mm. In one exemplary embodiment, angle α is substantially equal to 90 degrees. In this embodiment, ledge potion 58 is substantially perpendicular to longitudinal axis LA of intramedullary nail 30.

In one exemplary embodiment, runout portion 60 extends along longitudinal axis LA of intramedullary nail 30, through transition portion 36, and terminates at the proximal end of distal portion 34 of intramedullary nail 30. Specifically, in this embodiment, runout portion 60 is substantially coplanar with a plane tangent to a lateral most portion of distal portion 34 and parallel to longitudinal axis LA of intramedullary nail 30. In other exemplary embodiments, runout portion 60 extends into and terminates within distal portion 34. In these embodiments, runout portion 60 is not substantially coplanar with a plane tangent to a lateral most portion of distal portion 34, but may be substantially parallel to longitudinal axis LA of intramedullary nail 30. Alternatively, in other exemplary embodiments, runout portion 60 terminates within transition portion 36. For example, runout portion 60 may terminate at the periphery of transition portion 36 as described above with reference to the transition portion periphery. In exemplary embodiments, in order to alter the position at which runout portion 60 terminates distally, i.e., the distal most point of runout portion 60, runout portion 60 is maintained in a plane parallel to longitudinal axis LA of intramedullary nail 30 and is moved closer to or further away from longitudinal axis LA of intramedullary nail 30. In one example, the runout portion 60 is spaced from the longitudinal axis LA of the elongate body 30 by a distance at least as great as one-half of the distal diameter of the transition portion 36. In one example, the runout portion 60 is spaced from the longitudinal axis LA of the elongate body 30 by a distance greater than one-half of the distal diameter of the transition portion 36 and less than the proximal diameter of the transition portion 36, wherein the runout portion 60 terminates distally at the transition portion periphery.

By forming cutout 56 in intramedullary nail 30, material having a thickness T is positioned on the proximal side of lag screw 50 between runout portion 60 and the lateral-most surface of intramedullary nail 30 positioned proximal of lag screw 50, while a corresponding amount of material is removed from the distal side of lag screw 50. By removing material distally of lag screw 50, the stresses that are introduced in the material directly adjacent to the lateral opening of transverse bore 48, such as in the area distal of support point 54, and described in detail above, are distributed in a direction toward longitudinal axis LA of intramedullary nail 30. As a result, the stresses introduced in the material directly adjacent to the lateral opening of transverse bore 48 are distributed through a portion of intramedullary nail 30 where the material forming intramedullary nail 30 is thicker, i.e., through a portion of intramedullary nail 30 spaced a decreased lateral distance from longitudinal axis LA of intramedullary nail 30 relative to the material directly adjacent to the lateral opening of transverse bore 48. This allows for the concentration of the stresses in the area of the lateral opening of transverse bore 48 to be reduced, as the stresses are spread throughout the body of intramedullary nail 30.

As a result, intramedullary nail 30 may have a decreased thickness relative to known intramedullary nails while providing substantially similar or improved strength properties as compared to known intramedullary nails. For example, as indicated above, the diameter of proximal portion 38 of intramedullary nail 30 may be as small as 15.5 mm, while the diameter of a proximal portion of a comparable prior art intramedullary nail is 17 mm. Similarly, the diameter of transverse bore 48 of intramedullary nail 30 may be as small as 10.5 mm, while the diameter of the corresponding transverse bore of a comparable prior art intramedullary nail is 12 mm.

In order to further enhance the preferential stress distribution of intramedullary nail 30 of the present invention, flattened side surfaces 62, 64 may be formed on opposing sides of lateral opening 68 of transverse bore 48 as shown in FIG. 4B and described in detail above. Additionally, in the embodiment shown in FIGS. 4A and 4B, the lateral most point of ledge portion 58 defines support point 54. As a result, support point 54 is maintained in its relative position even in the presence of cutout 56.

Figure 5A:
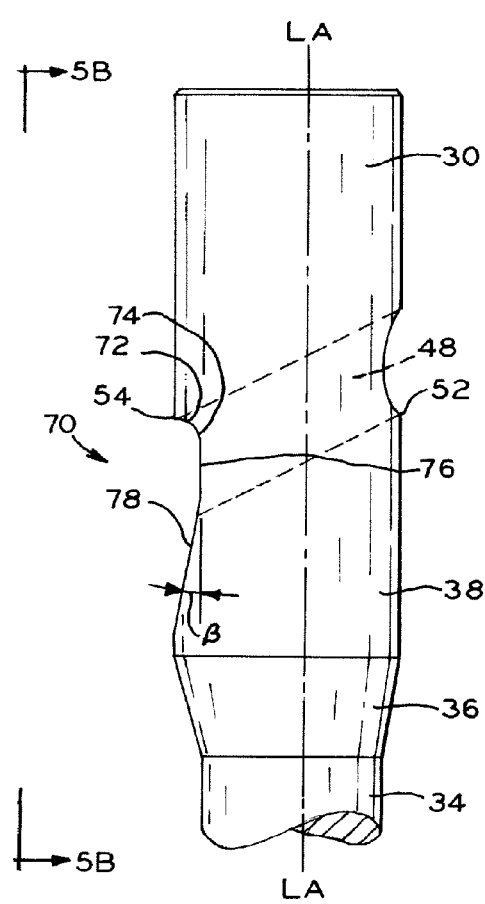
FIG. 5A is a fragmentary, side view of an intramedullary nail of the present invention according to another exemplary embodiment.
Figure 5B:
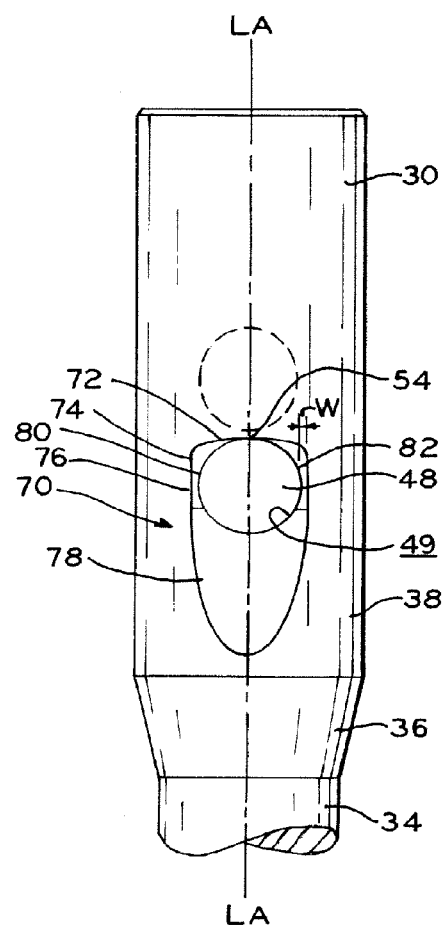
FIG. 5B is a fragmentary view of the intramedullary nail of FIG. 5A taken in the direction of line 5B-5B of FIG. 5A.

Referring to FIGS. 5A and 5B, another exemplary embodiment of a cutout formed in accordance with the teachings of the present invention is shown as cutout 70. Cutout 70 may be utilized with intramedullary nail 30 of FIGS. 8 and 9 and like reference numerals have been used to represent corresponding components therebetween. Referring to FIGS. 5A and 5B, cutout 70 includes ledge portion 72, intermediate portion 74, longitudinal portion 76, and ramp portion 78. Intermediate portion 74 connects ledge portion 72 to longitudinal portion 76. In one exemplary embodiment, intermediate portion 74 has a radius of curvature of approximately 3 mm.

Referring to FIGS. 5A and 5B, longitudinal portion 76 defines a substantially planar surface extending in a plane that is substantially parallel to longitudinal axis LA of intramedullary nail 30. In one exemplary embodiment, longitudinal portion 76 terminates at a point near, but proximal of, the distal most portion of the wall defining transverse bore 48. Stated another way, longitudinal portion 76 terminates before reaching the distal most portion of transverse bore 48. In a similar manner as runout portion 78 of cutout 70, longitudinal portion 76 defines flattened side surfaces 80, 82 adjacent to the anterior and posterior sides of transverse bore 48. In one exemplary embodiment, flattened side surfaces 80, 82 have a width W of at least 0.2 mm.

Ramp portion 78 of cutout 70 defines a substantially planar, oblique surface that extends distally from longitudinal portion 76. Ramp portion 78 forms angle β with longitudinal axis LA of intramedullary nail 30. Ramp portion 78 is oriented such that ramp portion 78 angles toward longitudinal axis LA of intramedullary nail 30 in a proximal direction and away from longitudinal axis LA of intramedullary nail 30 in a distal direction. In one exemplary embodiment, angle β is less than 45 degrees. In another exemplary embodiment, angle β is less than 30 degrees. In exemplary embodiments, angle β may be as small as approximately 0.0 degree (in which ramp portion 78 forms runout portion 78), 0.5 degree, 1 degree, 3 degrees, 5 degrees, or 10 degrees and as large as approximately 15 degrees, 20 degrees, 25 degrees, or 30 degrees. Additionally, the smaller that angle β is the closer ramp portion 78 is to being parallel to longitudinal axis LA of intramedullary nail 30. As a result, it is easier to form ramp portion 78 during the manufacturing process and the volume of the space provided for bone ingrowth is increased.

Figure 6A:
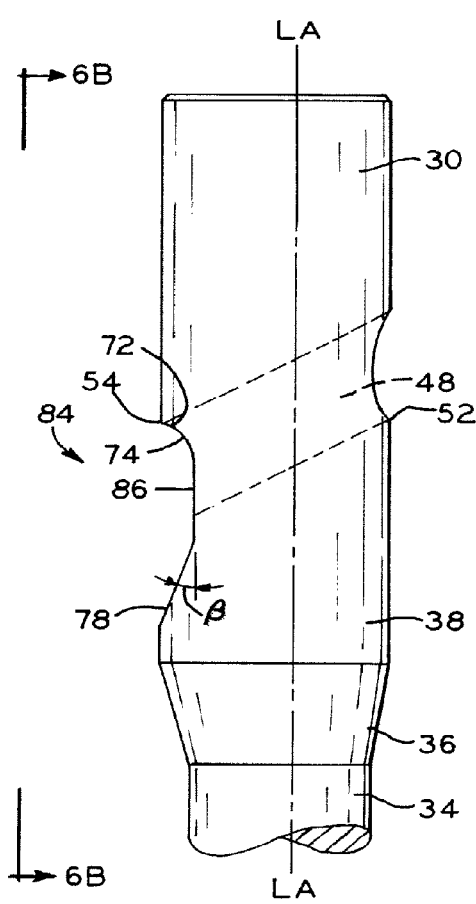
FIG. 6A is a fragmentary, side view of an intramedullary nail of the present invention according to another exemplary embodiment.
Figure 6B:
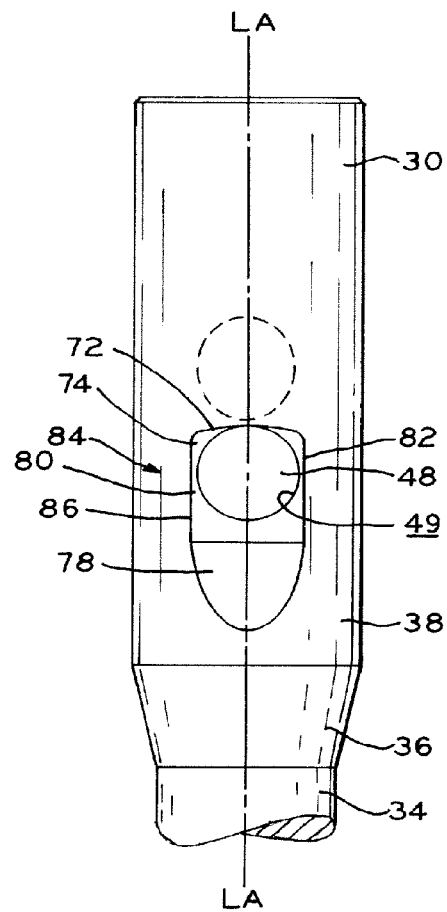
FIG. 6B is a fragmentary view of the intramedullary nail of FIG. 6A taken in the direction of line 6B-6B of FIG. 6A.

Referring to FIGS. 6A and 6B, another exemplary embodiment of a cutout formed in accordance with the teachings of the present invention is shown as cutout 84. Cutout 84 is substantially similar to cutout 70 of FIGS. 5A and 5B and may be utilized with intramedullary nail 30 of FIGS. 8 and 9 and like reference numerals have been used to represent identical or substantially identical components therebetween. In contrast to longitudinal portion 76 of cutout 70, longitudinal portion 86 of cutout 84 terminates at a point distal of the distal most portion of transverse bore 48. In another exemplary embodiment, longitudinal portion 86 may terminate at a point that coincides with the distal most point of transverse bore 48.

Referring to FIGS. 7A and 7B, another exemplary embodiment of a cutout formed in accordance with the teachings of the present invention is shown as cutout 32. Cutout 32 is substantially similar to cutout 70 of FIGS. 5A and 5B and like reference numerals have been used to identify identical or substantially identical components therebetween. Referring to FIGS. 7A and 7B, unlike cutout 70 of FIGS. 5A and 5B, no portion of cutout 32 is parallel to longitudinal axis LA of intramedullary nail 30 and cutout 32 lacks longitudinal portion 76. Thus, ledge portion 92 and ramp portion 94 of cutout 32 are connected to one another by intermediate portion 96 and are separated from one another by angle λ. In one exemplary embodiment, angle λ is substantially equal to 90 degrees. In one exemplary embodiment, intermediate portion 96 has a radius of curvature of approximately 3 mm. In one exemplary embodiment, ledge portion 92 is also curved. In one exemplary embodiment, ledge portion 32 has a radius of curvature of approximately 3 mm.

Alternatively, in another exemplary embodiment, ledge portion 92 may include a substantially planar portion. In one exemplary embodiment, a plane containing ledge portion 92 intersects the longitudinal axis of transverse bore 48 and is substantially perpendicular to longitudinal axis LA of intramedullary nail 30. Referring now to ramp portion 94, ramp portion 94 defines substantially planar surface 98 that tapers away from the longitudinal axis LA of intramedullary nail 30 in a distal direction to form angle ε (FIG. 7A) relative to longitudinal axis LA of intramedullary nail 30. In one exemplary embodiment, angle ε is 9 degrees. In another exemplary embodiment, angle ε is 10 degrees. In a further exemplary embodiment, angle ε is 6 degrees. In exemplary embodiments, angle ε may be any angle in the range of 4-12 degrees.

In exemplary embodiments, due to angles γ and angles ϵ (FIG. 7A), ledge portion 92 may form a slight angle relative to a line that is perpendicular to longitudinal axis LA of intramedullary nail 30. Thus, while ledge portion 92 may still remain substantially perpendicular to longitudinal axis LA, ledge portion 92 may form an angle δ (FIG. 7A) with longitudinal axis LA of intramedullary nail 30. Thus, in exemplary embodiments, instead of angle δ being 90 degrees from longitudinal axis LA and ledge portion 92 being perpendicular with longitudinal axis LA, angle δ will, for any particular embodiment, be equal to 180 degrees minus the sum of angle γ and angle ϵ. For example, when angle γ is 90 degrees and angle ϵ is 10 degrees, angle δ will be equal to 80 degrees.

In order to form any of cutouts 32, 56, 70, 84 in intramedullary nail 30, cutouts 32, 56, 70, 84 may be machined into intramedullary nail 30 by advancing a cutting tool having a radius substantially equal to the desired radius of intermediate portion 66, 74, 96 in a direction substantially transverse to longitudinal axis LA of intramedullary nail 30. In one exemplary embodiment, a longitudinal axis of the cutting tool is aligned perpendicularly to the longitudinal axis of transverse bore 48. In one exemplary embodiment, the movement of the cutting tool may be automatically controlled, such as by the use of a computer numerical control ("CNC") machine. Once the cutting tool has reached the desired depth, further movement of the cutting tool into, i.e., in a direction toward longitudinal axis LA of intramedullary nail 30, is stopped. By advancing a cutting tool having a radius of curvature substantially similar to the radius of curvature of intermediate portion 66, 74, 96 to the desired depth, both ledge portion 58, 72, 92 and intermediate portion 66, 74, 96 are created substantially simultaneously.

Then, in order to form longitudinal portion 76, 86 or runout portion 60, if required, the cutting tool is moved in a distal direction substantially parallel with longitudinal axis LA of intramedullary nail 30. Once the cutting tool has been advanced to the desired distal termination point of longitudinal portion 76, 86 or, for runout portion 60, out of the material forming intramedullary nail 30, ramp portion 78, 90 may be formed. Alternatively, if longitudinal portion 76, 86 is not required, such as for cutout 32, the step of forming longitudinal portion 76, 86 is skipped and ramp or runout portion 60, 78, 90 is formed directly after forming ledge portion 58, 72, 92 and intermediate portion 66, 74, 96.

In order to form ramp portion 78, 94, the cutting tool may be advanced from the desired depth in both a distal direction and a direction out of, i.e., away from the longitudinal axis LA of, intramedullary nail 30. Stated another way, the cutting tool is advanced away from longitudinal axis LA along a plane forming angle β, ϵ (FIGS. 5A, 7A) relative to longitudinal axis LA. The advancement of the cutting tool in this manner is continued until the cutting tool no longer contacts the material forming intramedullary nail 30. Once the cutting tool no longer contacts the material forming intramedullary nail 30, ramp portion 78, 94 is formed.

Alternatively, in another exemplary embodiment, in order to form ramp portion 78, 94 and/or longitudinal portion 76, 86, the cutting tool may be removed from intramedullary nail 30 after forming ledge portion 58, 72, 92, intermediate portion 66, 74, 96, and, in some embodiments, longitudinal portion 76, 86 and repositioned at a point that is at the desired distal most point of the cutout. The cutting tool may be advanced from this distal point in a direction that is both into, i.e., toward longitudinal axis LA, and proximal relative to intramedullary nail 30. Stated another way, the cutting tool is advanced toward longitudinal axis LA along a plane forming angle β, ϵ 8 (FIGS. 5A, 7A) with longitudinal axis LA. As the cutting tool continues to be advanced, the length and depth of ramp portion 78, 94 is correspondingly increased. The advancement of the cutting tool is stopped when the cutting tool is substantially adjacent and/or contacts intermediate portion 66, 74, 96 or a distal most point of longitudinal portion 76, 86. Then, if not yet formed, longitudinal portion 76, 86 may be formed by advancing the cutting tool in a proximal direction parallel with longitudinal axis LA of intramedullary nail 30.

In another exemplary embodiment, cutouts 32, 56 are machined into intramedullary nail 30 by advancing a cutting tool having a radius that is greater than the desired radius of intermediate portions 96, 66 from one of an anterior side and a posterior side of intramedullary nail 30 to the other of the anterior side and the posterior side of intramedullary nail 30. Specifically, referring to FIG. 7A and cutout 32, a longitudinal axis of the cutting tool is aligned to form angle ϵ with longitudinal axis LA of intramedullary nail 30. Then, the cutting tool is positioned at one of the anterior or posterior sides of intramedullary nail 30 with the tip of the cutting tool advanced to a proximal position equal to the desire proximal most point of ledge portion 92. The cutting tool is then advanced across the lateral side of intramedullary nail 30 to the opposing anterior or posterior side and ledge portion 92 and ramp portion 94 of cutout 32 are formed. Additionally, by using a standard cylindrical cutting tool, ledge portion 92 may be formed with angle γ (FIG. 7A) being substantially equal to ninety degrees. Once ledge portion 92 and ramp portion 94 are formed, an additional machining step, such as one of the steps described in detail above, is needed to form intermediate portion 96. In one exemplary embodiment, the movement of the cutting tool may be automatically controlled, such as by the use of a computer numerical control ("CNC") machine. Advantageously, by forming cutouts 32, 56 by using a cutting tool having a diameter greater than the desired diameter of intermediate portions 96, 66 and by advancing the cutting tool across intramedullary nail 30 instead of along the longitudinal axis LA of intramedullary nail 30, less vibration is generated in intramedullary nail 30 during the formation of cutouts 32, 56.

In other exemplary embodiments, cutouts 32, 56, 70, 84 may be formed in intramedullary nail 30 by casting, forging, or other known manufacturing techniques.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An intramedullary nail, comprising:
   an elongate body including a proximal end defined by a proximal portion, a distal end defined by a distal portion, a medial side, a lateral side, and a longitudinal axis, said elongate body defining an elongate body periphery, said proximal portion of said elongate body having an interior wall defining a transverse bore extending therethrough, said transverse bore extending from said lateral side to said medial side of said elongate body in a direction transverse to said longitudinal axis of said elongate body, said proximal portion including a cutout positioned adjacent to said transverse bore on said lateral side of said elongate body, said cutout comprising:
a ledge portion extending in a substantially medial-lateral direction and positioned adjacent to a proximal most edge of said wall defining said transverse bore;
a ramp portion defining a substantially planar surface, said ramp portion forming a ramp angle with said longitudinal axis of said elongate body, said ramp angle being between zero degrees and thirty degrees, wherein said ramp portion extends along the longitudinal axis of the elongate body in a distal direction, said ramp portion terminating distally at said elongate body periphery, wherein said ramp portion terminates at a position spaced distally from a distal most edge of said wall defining said transverse bore; and
an intermediate portion positioned between said ledge portion and said ramp portion, said intermediate portion having an intermediate portion radius of curvature;
wherein said ramp portion defines a runout portion defining a substantially planar surface, said runout portion extending in a plane substantially parallel to both said longitudinal axis of said elongate body and a plane tangent to said elongate body periphery at a lateral point of said proximal portion; and
wherein said elongate body further comprises a transition portion extending proximally from said distal portion along said longitudinal axis, said transition portion having a proximal end having a proximal diameter and a distal end having a distal diameter, said proximal diameter being greater than said distal diameter, wherein said runout portion is spaced from said longitudinal axis of said elongate body by a distance greater than one-half of said distal diameter of said transition portion and less than said proximal diameter of said transition portion, wherein said runout portion terminates distally at said transition portion periphery.

2. The intramedullary nail of claim 1, wherein said cutout further comprises a longitudinal portion extending between said intermediate portion and said ramp portion, said longitudinal portion defining a substantially flat surface extending substantially parallel to said longitudinal axis of said elongate body.

3. The intramedullary nail of claim 2, wherein said longitudinal portion terminates distally at a position between a proximal most edge of said wall defining said transverse bore and a distal most edge of said wall defining said transverse bore.

4. The intramedullary nail of claim 2, wherein said longitudinal portion terminates distally at a position spaced distally from a distal most edge of said wall defining said transverse bore.

5. The intramedullary nail of claim 2, wherein said longitudinal portion defines flattened side surfaces on opposing anterior and posterior sides of said transverse bore, each of said flattened side surfaces having a width of at least substantially two millimeters.

6. The intramedullary nail of claim 1, wherein at least a portion of said ledge portion is positioned no more proximally than a proximal most portion of said wall defining said transverse bore, wherein said ledge portion defines a lateral support point for a lag screw received within said transverse bore of said elongate body.

7. The intramedullary nail of claim 1, wherein said ramp portion defines flattened side surfaces on opposing anterior and posterior sides of said transverse bore, each of said flattened side surfaces having a width of at least substantially two millimeters.

8. The intramedullary nail of claim 1, wherein said ledge portion forms a separation angle with said ramp portion, said separation angle being equal to substantially ninety degrees.

9. An intramedullary nail, comprising:
an elongate body including a proximal end defined by a proximal portion, a distal end defined by a distal portion, a medial side, a lateral side, and a longitudinal axis, said elongate body defining an elongate body periphery, said proximal portion of said elongate body having an interior wall defining a transverse bore extending therethrough, said transverse bore extending from said lateral side to said medial side of said elongate body in a direction transverse to said longitudinal axis of said elongate body, said proximal portion including a cutout positioned adjacent to said transverse bore on said lateral side of said elongate body, said cutout comprising:
a ledge portion extending in a substantially medial-lateral direction and positioned adjacent to a proximal most edge of said wall defining said transverse bore;
a ramp portion defining a substantially planar surface, said ramp portion forming a ramp angle with said longitudinal axis of said elongate body, said ramp angle being between zero degrees and thirty degrees, wherein said ramp portion extends along the longitudinal axis of the elongate body in a distal direction, said ramp portion terminating distally at said elongate body periphery, wherein said ramp portion terminates at a position spaced distally from a distal most edge of said wall defining said transverse bore; and
an intermediate portion positioned between said ledge portion and said ramp portion, said intermediate portion having an intermediate portion radius of curvature, wherein said ramp portion defines a runout portion defining a substantially planar surface, said runout portion extending in a plane substantially parallel to both said longitudinal axis of said elongate body and a plane tangent to said elongate body periphery at a lateral point of said proximal portion, wherein said elongate body further comprises a transition portion extending proximally from said distal portion along said longitudinal axis, said transition portion having a proximal end having a proximal diameter and a distal end having a distal diameter, said proximal diameter being greater than said distal diameter, wherein said runout portion is spaced from said longitudinal axis of said elongate body by a distance at least as great as one-half of said distal diameter of said transition portion, and wherein said distal portion has a distal portion periphery and said runout portion is substantially coplanar with a plane tangent to said distal portion periphery at a proximal most point of said distal portion periphery, whereby said runout portion terminates distally at said distal portion periphery.

10. The intramedullary nail of claim 9, wherein said ledge portion forms a separation angle with said runout portion, said separation angle being equal to substantially ninety degrees.

11. The intramedullary nail of claim 9, wherein at least a portion of said ledge portion is positioned no more proximally than a proximal most portion of said wall defining said transverse bore, wherein said ledge portion defines a lateral support point for a lag screw received within said transverse bore of said elongate body.

12. The intramedullary nail of claim 9, wherein said runout portion defines flattened side surfaces on opposing anterior and posterior sides of said transverse bore, each of said flattened side surfaces have a width of at least substantially two millimeters.

* * * * *